United States Patent
Maldon Ado Bas

(10) Patent No.: US 7,811,268 B2
(45) Date of Patent: Oct. 12, 2010

(54) DEVICE FOR DRAINING AQUEOUS HUMOR IN CASES OF GLAUCOMA

(75) Inventor: Arturo Maldon Ado Bas, Córdoba (AR)

(73) Assignee: Artom S.A., Buenos Aires (AR)

( * ) Notice: Subject to any disclaimer, the term of this patent is extended or adjusted under 35 U.S.C. 154(b) by 554 days.

(21) Appl. No.: 11/354,529

(22) Filed: Feb. 15, 2006

(65) Prior Publication Data

US 2006/0189916 A1    Aug. 24, 2006

(30) Foreign Application Priority Data

Feb. 21, 2005 (AR) ............................... P050100621

(51) Int. Cl.
*A61M 35/00* (2006.01)
(52) U.S. Cl. ............................... 604/294; 604/8; 604/9
(58) Field of Classification Search .................. 604/361, 604/362, 294, 8, 9
See application file for complete search history.

(56) References Cited

U.S. PATENT DOCUMENTS

| | | | |
|---|---|---|---|
| 3,915,172 A | 10/1975 | Wichterle et al. | |
| 4,037,604 A | 7/1977 | Newkirk | |
| 4,457,757 A | 7/1984 | Molteno | |
| 4,604,087 A | 8/1986 | Joseph | |
| 4,750,901 A | 6/1988 | Molteno | |
| 4,886,488 A | 12/1989 | White | |
| 4,936,825 A | 6/1990 | Underleider | |
| 4,968,296 A | 11/1990 | Ritch et al. | |
| 5,041,081 A | 8/1991 | Odrich | |
| 5,127,901 A | 7/1992 | Odrich | |
| 5,178,604 A | 1/1993 | Baerveldt et al. | |
| 5,397,300 A | 3/1995 | Baerveldt et al. | |
| 5,411,473 A * | 5/1995 | Ahmed | 604/8 |
| 5,476,445 A * | 12/1995 | Baerveldt et al. | 604/8 |
| 5,486,165 A | 1/1996 | Steggmann | |
| 5,520,631 A | 5/1996 | Nordquist et al. | |
| 5,558,629 A | 9/1996 | Baerveldt et al. | |

(Continued)

FOREIGN PATENT DOCUMENTS

AU    728354 B    1/2001

(Continued)

OTHER PUBLICATIONS http://ecatalog.ethicon.com/sutures-non-absorbable/view/mersilene-suture PDF of catalogue page attached.*

*Primary Examiner*—Patricia M Bianco
*Assistant Examiner*—Ginger T Chapman
(74) *Attorney, Agent, or Firm*—Bachman & LaPointe, P.C.

(57) ABSTRACT

A device is made up of one piece, or two independent pieces, that can be linked with each other to make a unit. The anterior end of a drainage tube is introduced 2 mm into the anterior chamber of the eye while the rear end of the tube is placed in the scleral lake. A cover is a plane body slight in height and oval or oblong in format that is provided with four parallel cuts that create two girths. The said girths are used to retain the drainage tube below the cover, thus creating a curvature in it to form a concave inner surface and a convex outer surface.

15 Claims, 2 Drawing Sheets

U.S. PATENT DOCUMENTS

| | | | |
|---|---|---|---|
| 5,558,630 A | 9/1996 | Fisher | |
| 5,616,118 A * | 4/1997 | Ahmed | 604/8 |
| 5,626,558 A * | 5/1997 | Suson | 604/8 |
| 5,681,275 A * | 10/1997 | Ahmed | 604/9 |
| 5,722,948 A * | 3/1998 | Gross | 604/8 |
| 5,752,928 A | 5/1998 | de Roulhac | |
| 5,882,327 A * | 3/1999 | Jacob | 604/8 |
| 6,007,510 A * | 12/1999 | Nigam | 604/8 |
| 6,142,969 A | 11/2000 | Nigam | |
| 6,186,974 B1 | 2/2001 | Allan | |
| 6,508,779 B1 | 1/2003 | Suson | |
| 6,544,208 B2 * | 4/2003 | Ethier et al. | 604/8 |
| 6,544,249 B1 | 4/2003 | Yu | |
| 6,589,203 B1 * | 7/2003 | Mitrev | 604/27 |
| 6,730,056 B1 | 5/2004 | Ghaem et al. | |
| 6,881,197 B1 | 4/2005 | Nigam | |
| 6,962,573 B1 * | 11/2005 | Wilcox | 604/9 |
| 2001/0053873 A1 | 12/2001 | Schaaf et al. | |
| 2002/0013545 A1 | 1/2002 | Soltanpour et al. | |
| 2002/0026200 A1 | 2/2002 | Savage | |
| 2002/0087111 A1 | 7/2002 | Ethier et al. | |
| 2003/0153863 A1 | 8/2003 | Patel | |
| 2003/0236483 A1 | 12/2003 | Ren | |
| 2004/0015140 A1 | 1/2004 | Shields | |
| 2004/0092856 A1 | 5/2004 | Dahan | |
| 2004/0210181 A1 | 10/2004 | Vass et al. | |
| 2005/0182350 A1 * | 8/2005 | Nigam | 604/8 |
| 2005/0267397 A1 * | 12/2005 | Bhalla | 604/8 |
| 2005/0267398 A1 * | 12/2005 | Protopsaltis et al. | 604/8 |
| 2006/0155238 A1 * | 7/2006 | Shields | 604/8 |

FOREIGN PATENT DOCUMENTS

| | | |
|---|---|---|
| CN | 2414757 Y | 1/2001 |
| EP | 168201 | 1/1986 |
| FR | 2553658 | 4/1985 |
| GB | 2101891 | 1/1983 |
| GB | 2187963 | 9/1987 |
| JP | 608788 | 3/1994 |
| JP | 2001245916 | 9/2001 |
| JP | 2004208898 | 7/2004 |
| MX | 05000807 | 6/2005 |
| NZ | 337059 | 4/2001 |
| RU | 2204969 | 5/2003 |
| SU | 1805938 | 3/1993 |
| WO | WO8900869 | 2/1989 |
| WO | WO9219294 | 11/1992 |
| WO | WO9320783 | 10/1993 |
| WO | WO9400837 | 5/1994 |
| WO | WO9417755 | 8/1994 |
| WO | WO9603944 | 2/1996 |
| WO | WO9620742 | 7/1996 |
| WO | WO9850092 | 11/1998 |
| WO | WO9966862 | 12/1999 |
| WO | WO0006223 | 2/2000 |
| WO | WO0232343 | 4/2002 |
| WO | WO02080829 | 10/2002 |
| WO | WO02087418 | 11/2002 |
| WO | WO03099175 | 12/2003 |
| WO | WO2004060219 | 7/2004 |
| WO | WO2004064694 | 8/2004 |
| WO | WO2004073552 | 9/2004 |
| WO | WO2004073564 | 9/2004 |
| WO | WO2005046782 | 5/2005 |

* cited by examiner

DEVICE FOR DRAINING AQUEOUS HUMOR IN CASES OF GLAUCOMA

BACKGROUND OF THE INVENTION (1.) Field of the Invention

The present invention consists of a device for draining aqueous humor in cases of glaucoma.

(2.) Prior Art

Glaucoma is a disease of the eyes, so-called from the greenish tinge acquired by the pupil, the main signs of which are an increase in intraocular pressure, leading to atrophy of the optic disk, hardening of the ocular globe, and finally blindness.

The increase in intraocular pressure that normally arises in the production of a glaucoma occurs as a consequence of a dysfunction by which the aqueous humor produced by the ciliary body exceeds the capacity of the trabecular network to eliminate it.

The increase in intraocular pressure is what medicine aims to correct in order to control the disease.

One of the most advanced surgical techniques for this purpose is Stegman's viscocanalostomy, or one of its variants such as the deep sclerectomy used by Mermoud and by Sourdille.

Both professionals seek to keep the intrascleral filtration space open by the use of a device, which, in Mermoud's case, consists of using pig collagen, while Sourdille prefers the use of hyaluronic acid.

Such devices leave an intrascleral filtration lake some 100 to 150 microns deep by some 400 microns in width, and thus permits intraocular pressure to be adequately regulated.

These are effective solutions for maintaining the intrascleral space, but they are also temporary, since with time they are reabsorbed.

SUMMARY OF THE INVENTION

In accordance with the present invention, a technique is performed that involves the ablation of the blocked filtration zone with excimer laser, instead of doing this manually.

In successful cases with any of the aforementioned techniques, it is possible to show through an ultrabiomicroscopy (UBM) study that said aqueous humor in the anterior chamber filters towards said intrascleral fitration space from which it is absorbed.

It should be remembered then that said intrascleral lake is separated from the anterior chamber by a distance of no more than 20 microns, occupied by the layer of trabecular fibers and the Descemet's membrane, through which the aqueous humor occupying said anterior chamber drains, pushed by the intraocular pressure, towards the intrascleral filtration space.

After surgery, therefore, two spaces or chambers are found, one of them, the anterior chamber of the eye, which has the greater hydrostatic pressure, while the second, intrascleral chamber, has no measurable pressure and is that from which, by means of the scleral vessels, the aqueous humor is drained.

Consistently with the laws of physics, the aqueous humor contained in the chamber with the higher pressure (the aforementioned anterior chamber of the eye) filters through a permeable membrane, pushed by the difference of pressures, towards a space (intrascleral chamber or space) from which it is absorbed.

In the Argentine patent application no. P030101745, by the same applicant, the possibility is mentioned of connecting the anterior chamber of the eye with the intrascleral space or scleral uvea (superciliary) from which the aqueous humor can be evacuated.

In said application, it is also mentioned the possibility of using the suprachoroidal space in combination with the intrascleral or, as an alternative, using only the latter, connecting it to the anterior chamber with a device of his own authorship developed for this purpose.

The object of said application was improved in the Argentine patent application no. P030101897, in the presentation of which the applicant progresses one step in the treatment of glaucoma, designing a microdevice that enables the scleral filtration space to be kept open, and for this purpose links the anterior chamber of the eye, containing the aqueous humor, with a scleral filtration space via a tube.

To prevent the scleral flap collapsing and the later cicatrization interrupting the communication between the anterior chamber of the eye and the scleral lake, a plate is provided above said tube, as a cover, the exterior surface of which is convex and the interior surface of which is concave.

Said plate contains orifices for sutures to pass and is fixed next to the limbus, maintaining the scleral filtration space permanently open, so that the microdevice constitutes a system of communicating vessels between the anterior chamber of the eye with its positive hydrostatic pressure and the scleral filtration space that has no measurable pressure.

Said patent application from the applicant are therefore the current state of the technique referred to in the present documentation.

Even though the microdevice can be manufactured in a single piece, the difficulties presented by such a development have led to the present invention, as an alternative to the previous, solving and also eliminating the difficulties that the very small dimensions of these devices presented for their manufacture and placing.

A device is made up of one piece, or two independent pieces, that can be linked with each other to make a unit. The anterior end of a drainage tube is introduced 2 mm into the anterior chamber of the eye while the rear end of the tube is placed in the scleral lake. A cover is a plane body slight in height and oval or oblong in format that is provided with four parallel cuts that create two girths. The said girths are used to retain the drainage tube below the cover, thus creating a curvature in it to form a concave inner surface and a convex outer surface.

In order to make this invention comprehensible and enable it to be put into operation without difficulties, the following will be a precise description of only one preferred way of realizing it.

Reference will be made to the drawings that illustrate and accompany the description as examples of said way of realizing it, but neither the description nor the diagrams should be considered as limiting the invention.

The components explained may be selected by experts in the subject from among multiple equivalents, without this implying a deviation from the principles established in the present documentation.

BRIEF DESCRIPTION OF THE DRAWINGS

In the accompanying drawings.

DETAILED DESCRIPTION OF THE PREFERRED EMBODIMENT(S)

Figure 1:
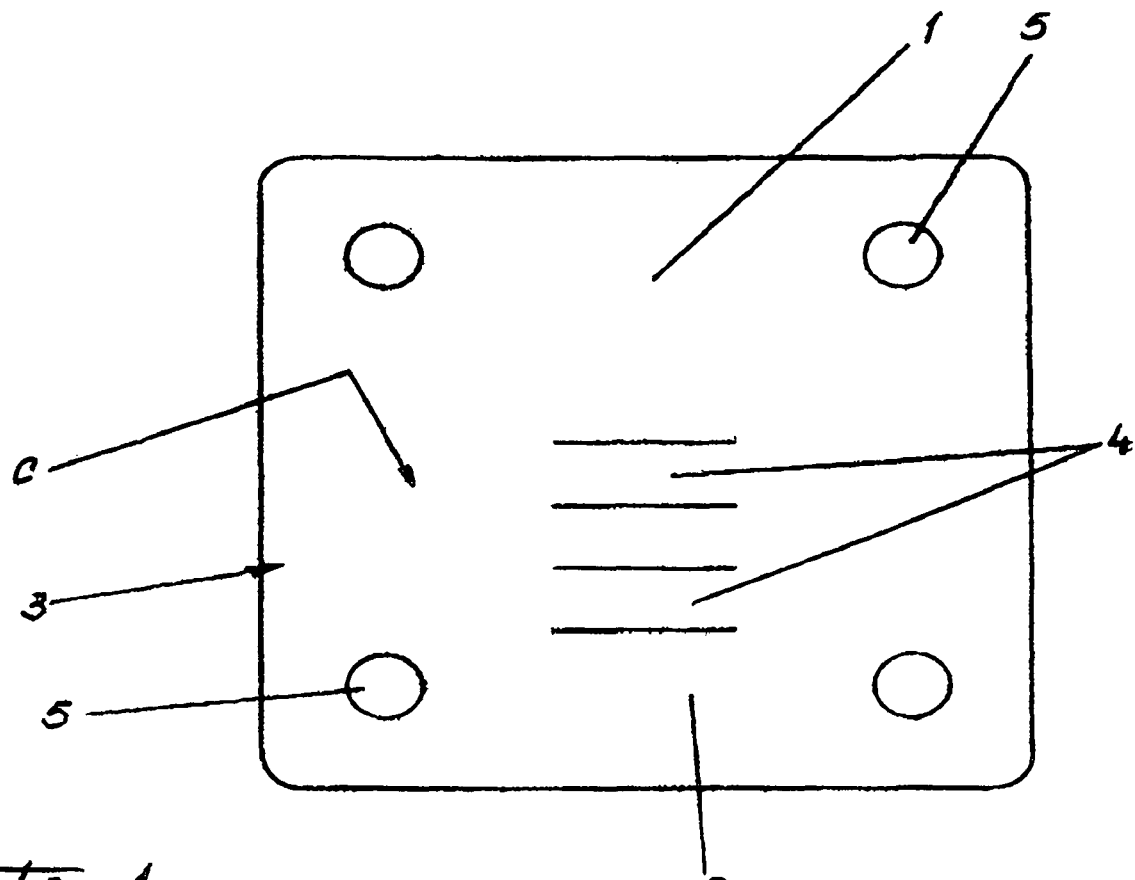
FIG. 1 represents a view from above of the cover of the present invention.
Figure 2:
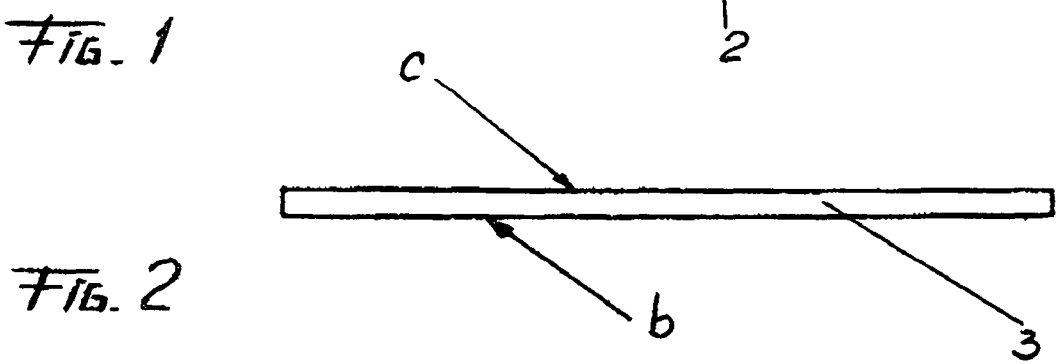
FIG. 2 shows a front view of the cover.
Figure 3:
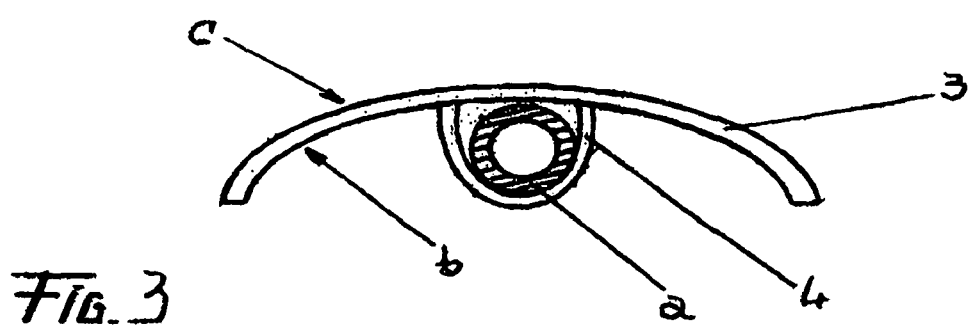
FIG. 3 shows a similar view to the previous, in which the drainage tube is incorporated. In this figure the girths can be seen, and the way in which the cover bends as a result of incorporating said drainage tube.
Figure 4:
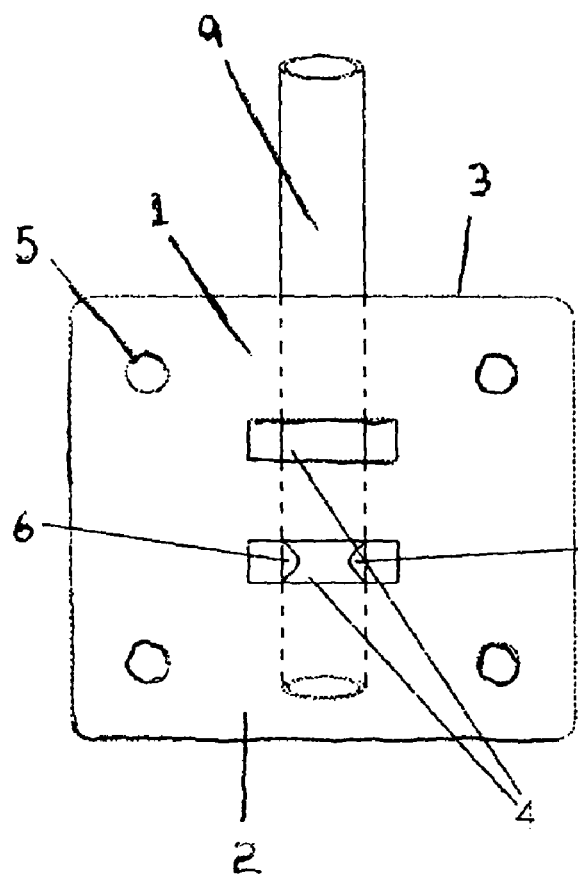
FIG. 4 is a lateral view of the cover in which the drainage tube is incorporated.
Figure 5:
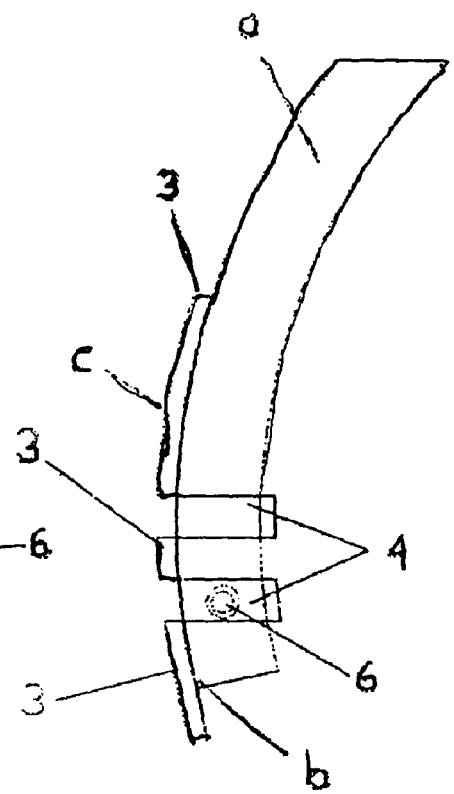
FIG. 5 is a lateral view of the cover in which the drainage tube is incorporated.

In the above-mentioned figures, identical reference characters indicate identical or corresponding parts, with number -1- an anterior end; number -2- a rear end; number -3- a cover; number -4- a girth; number -5-a perforation; and number -6- an orifice.

The letter -a- is reserved to indicate a drainage tube; the letter -b- to indicate an inner surface and letter -c- to indicate an outer surface.

Basically, the present invention refers to a device for draining the aqueous humor in cases of glaucoma, consisting of a tube of biocompatible material, circular or oval in form, on which a cover is provided that can be assembled with the former.

The device is complemented with a means for fixing the two portions.

Having established the different components of the version of the invention, shown in order to explain their nature, this description is now complemented with the functional and operational explanation of its parts and of the result they provide.

As a direct consequence of the small dimensions of the device, its manufacture in one piece presents the difficulty of making a matrix to be injected.

Tests carried out have led to the conclusion that with the aim of obtaining a device for draining aqueous humor in cases of glaucoma, an ideal option is to make it of two independent pieces and, for this, the first piece consists of a drainage tube -a- that consists of a hollow body, preferably circular or oval in section.

Said drainage tube (a) has its anterior end -1- linked to the anterior chamber of the eye or containing chamber of aqueous humor, and its rear end -2- linked to a scleral filtration space or scleral lake.

In order to prevent cicatrization with its consequent interruption of the communication formed by the drainage tube (a), a cover -3- is placed over this, preferably made of said biocompatible material.

This cover (3) is the only piece that must definitely be made from the matrix.

It therefore remains to establish the way or the means that enable said drainage tube (a) to be linked with said cover (3).

Said cover (3) consists of a flat body of little height and oval or oblong in shape, provided with four parallel cuts that form two girths -4- through which the drainage tube (a) can be threaded.

Situating the drainage tube (a) between said girths (4) and the lower face of the cover (3), the latter bends leaving an inner surface -b- concave downwards and an outer surface -c- convex.

Said girths (4) retain the drainage tube (a) below the cover (3) and leave a space that enables the circulation of aqueous humor from the lower part to the upper part, thus forming two spaces of aqueous humor as has been demonstrated by ultra-biomicroscopy.

As a result, the anterior end (1) of the drainage tube (a) is put in communication with the anterior chamber of the eye while the rear end (2) is put in communication with the scleral filtration space or scleral lake.

Displaced towards the rear end (2) of the drainage tube (a) a cover (3) is provided which, when in place, presents its outer surface (c) convex and its inner surface (b) concave.

When the proposed invention is implanted, said rear end (2) and cover (3) remain located under the scleral flap.

In order to achieve efficient drainage of the aqueous humor with the aim of controlling the glaucoma, it has been necessary to develop an adequate surgical technique for implanting the device described.

For this reason, it is preferable to make a 7 mm fornix-based conjunctival incision, and a limbus-based laminar scleral flap of approximately 6 mm by 8 mm and 350 micras in depth.

At this point, one of two variants may be chosen.

The first variant results from making a paracentesis in front of Schwalbe's line, through which the device is introduced.

In this way, parallel to the iris, 2 mm of the anterior end (1) are introduced into the anterior chamber of the eye while the cover (3), that is displaced and covering the rear end (2) of the drainage tube (a) is situated next to the limbus and it is then fixed with four non-reabsorbable sutures of polypropylene or mersilene 9 or 10-0.

Lastly the scleral flap is replaced and sutured with nylon 9-0 stitches and the conjunctiva is also sutured with silk 8-0.

The second of the options mentioned consists in, once the scleral flap has been made, making a 1.5 mm vertical incision, extending it to the supraciliary space, 2 mm from the limbus.

Through said incision a cyclodialysis is performed, introducing 2 mm of the anterior portion (1) of the drainage tube (a) into the uveoscleral space and 2 mm into the anterior chamber of the eye, parallel to the iris.

The cover (3), including the rear portion (2) is fixed 2 mm from the limbus with non-reabsorbable sutures such as polypropylene or MERSILENE® Polyester Fiber Suture by Ethicon 9 or 10-0, to end the surgery with the scleral and conjunctival suturing.

It is preferable that the cover (3) be provided with the perforations -5- necessary for passing the sutures for ease of operation.

With the described technique, in the first option, a communication is made between the anterior chamber of the eye and the intrascleral space (b) through the tube that, as was mentioned, is hollow. Through the openings of the cuts in the cover, aqueous humor can circulate from the concave lower part towards the convex upper part, creating two spaces of aqueous humor to improve filtration.

In this option, the cover (3) acts to maintain the intrascleral space in a similar way to that attained with the Mermoud and Sourdille techniques described.

However, different from them, there is used a drainage tube (a) and a cover (3) made of a non-degradable material, in such a way that the scleral filtration space is maintained permanently.

In the second option, a cyclodialysis is used in which the anterior end (1) of the drainage tube (a) is situated approximately 2 mm behind the limbus and in the supraciliary space, and the drainage tube (a) enters 2 mm into the anterior chamber.

Both the cover (3) and the rear portion (2) are fixed further behind.

In the manner described, two mechanisms are being used for the filtration, i.e. the supraciliary uveoscleral route and the intrascleral filtration space, forming a system of communicating vessels.

As has been described and diagrammed, the present invention consists of a device made up of a drainage tube (a) that consists of a hollow tubular body comprising an anterior end (1) and a rear end (2), together with a cover (3) consisting of a laminar body that is located displaced backwards so that it covers part of said rear end (2).

It has also been indicated that said drainage tube (a) is preferably circular or oval in section and presents an anterior end (1) placed in the anterior chamber of the eye and a rear end (2) on which said cover is located (3).

In consequence, said rear end (2) is defined as of a size that fits within the area covered by the perimeter of said cover (3).

As explained, the aqueous humor contained in the anterior chamber of the eye passes through the two ends (1 and 2) of the drainage tube (a), and, more concretely, from the anterior end (1) towards the rear end (2) reaching the scleral filtration space from which it is drained.

Preferably, the drainage tube (a) described has an outer diameter of between 0.5 mm and 1 mm and an inner diameter of between 0.3 mm and 0.4 mm.

In the preferred manner of making it, the rear end (2) of the drainage tube (a), located below the cover (3) may have two orifices 6 set in the sides.

Said orifices 6 present a diameter of approximately 0.3 mm by which means the filtration capacity of the device is increased.

The cover (3) preferably consists of a laminar body the outer surface of which (c) is convex while its inner surface (b) is concave.

Said cover (3) has a surface contained within a radius of between 2 mm and 3 mm.

Said cover (3) has a thickness of approximately 0.2 to 0.5 mm and the maximum height of the vault defined between the support plane and the highest point of the interior surface (b) is of between 0.4 mm and 0.7 mm.

In this way, the rear end (2) of the drainage tube (a) remains located below the cover (3) and within an open space which, in contrast to that seen in previous techniques, such as those previously explained of Mermoud and Sourdille, will not be absorbed and thus the scleral filtration space is maintained permanently.

It has been shown through ultrabiomicroscopy (UBM) that a filtration lake is also formed above the cover (3) below the scleral flap.

In practice, the cover (3) acts to maintain the scleral filtration space open and prevents the collapse of the scleral flap as well as the subsequent cicatrization and thus the closure of the scleral filtration space, creating at the same time a system of communicating vessels in which the greater pressure in one of them (i.e. the anterior chamber of the eye) forces the passage of the aqueous humor towards the other (scleral filtration space) where it is absorbed. A space is also seen above the cover (3) containing aqueous humor, which forms another route for its reabsorption.

It is highly important to stress that, in contrast to the valves used in prior techniques, the device described is fixed less than 10 mm from the limbus. This implies that, if retinal surgery should be needed in which a circular implant in the equator is used (approximately 14 mm from the limbus), the device presented will not interfere with said surgery.

The present invention is made with a biocompatible material such as silicon, hydroxyethylmetacrylate, hydrophobic acrylic or other.

Even though the present application refers to two pieces that constitute the invention, both of which are clearly differentiated from each other, it should be borne in mind that such reference is only in order to achieve a clear description since, once these are assembled, the aforementioned pieces constitute a unit, and can also be manufactured as a single piece.

The foregoing is a sketch of one of the possibilities of construction to put the invention into effect and of the manner in which it functions, and the application is now complemented with the synthesis of the invention contained in the following claims clauses.

What is claimed is:

1. A drainage device for implanting into a sclera of a patient's eye to drain aqueous humor from an anterior chamber of the eye into an intrascleral space the device comprising:
    a tube having a free anterior end at the anterior chamber of the eye and a free rear end at the intrascleral space; and
    a cover having a plurality of cuts forming girths, wherein the tube passes through the girths and is retained between the girths and a lower face of the cover, in a manner that the cover bends around the tube to leave an inner concave surface, whereby, with the tube passing through the girths, the anterior and rear ends of the tube remain free and the cuts in the cover are open to enable circulation of aqueous humor from a lower part to an upper part of the cover.

2. The device, according to claim 1, wherein the cover has a surface within a radius of between 2 mm and 3 mm, a thickness of approximately 0.2 to 0.5 mm and a maximum height of a vault defined between a supporting plane and a highest point of the inner surface of between 0.4 mm and 0.7 mm.

3. The device, according to claim 1, wherein the tube has an outer diameter of between 0.5 mm and 1 mm; an inner diameter of between 0.3 mm and 0.4 mm and sufficient length to position the anterior end in the anterior chamber of the eye and the rear end having a size which fits within an area covered by a perimeter of the cover, located in the intrascleral space for drainage of the aqueous humor.

4. The device, according to claim 1, wherein the tube has two lateral orifices in a zone next to the rear end, each orifice having a diameter of approximately 0.3 mm.

5. The device, according to claim 1, wherein lateral zones of the cover have a number of orifices suitable for passing sutures.

6. The device, according to claim 1, wherein at least one of said tube and cover is made of at least one non-degradable and biocompatible material.

7. The device according to claim 6, wherein the at least one non-degradable and biocompatible material is selected from the group consisting of silicon, hydroxyethylmetacrylate, and hydrophobic acrylic.

8. The device, according to claim 1, wherein the cover is fixed with four non-reabsorbable suture stitches of polypropylene or polyester fiber suture 9 or 10-0, the scleral flap is replaced with sutures of nylon 9-0, and the conjunctiva is sutured with silk 8-0.

9. The device, according to claim 1, wherein the device is fixed at less than 10 mm from the limbus.

10. A method of treating glaucoma by implanting a drainage device for aqueous humor in a patient's eye, the method comprising the steps of:
    providing a drainage device comprising a tube having a free anterior end and a free rear end, and a cover having cuts forming girths, wherein the tube passes through the girths and is retained between the girths and a lower face of the cover, in a manner that the cover bends around the tube to leave an inner concave surface, whereby, with the tube passing through the girths, the anterior and rear ends of the tube remain free and the cuts in the cover are open to enable circulation of aqueous humor from a lower part to an upper part of the cover;

making a fornix-based conjunctival incision, and a limbus-based laminar scleral flap;

inserting the cover with the tube into a sclera of the eye in a manner that the free end of the tube is placed into an anterior chamber of the eye and the free rear end into the sclera of the eye, ending into an intrascleral space, suturing the cover to the sclera, and closing and suturing the scleral flap.

11. The method of claim 10, wherein the step of making comprises making a 7 mm fornix-based conjunctival incision, and a limbus-based laminar scleral flap of about 6 mm by 8 mm and 350 micras in depth.

12. The method of claim 10, further comprising the step of making a paracentesis in front of Schwalbe's line, through which the device is introduced.

13. The method of claim 12, further comprising the step of taking a length of 2 mm of the free anterior end of the tube and introducing the end, parallel to the iris, into the anterior chamber of the eye while the cover, that is displaced and covering the free rear end of the tube, is situated next to a limbus of the eye and fixed with sutures, and replacing and suturing the scleral flap.

14. The method of claim 13, further comprising the step of performing a cyclodialysis, introducing 2 mm of the free anterior end of the tube into an uveoscleral space, and 2 mm into the anterior chamber of the eye, parallel to the iris.

15. The method of claim 10, wherein the step of making comprises making a 1.5 mm vertical incision, extending it to the supraciliary space, 2 mm from a limbus of the eye.

* * * * *